United States Patent
Ameri

(10) Patent No.: US 8,335,572 B2
(45) Date of Patent: Dec. 18, 2012

(54) MEDICAL DEVICE LEAD INCLUDING A FLARED CONDUCTIVE COIL

(75) Inventor: Masoud Ameri, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 70 days.

(21) Appl. No.: 12/843,573

(22) Filed: Jul. 26, 2010

(65) Prior Publication Data

US 2011/0087299 A1    Apr. 14, 2011

Related U.S. Application Data

(60) Provisional application No. 61/249,738, filed on Oct. 8, 2009.

(51) Int. Cl.
*A61N 1/05*    (2006.01)

(52) U.S. Cl. ......... 607/120; 607/115; 607/116; 607/119

(58) Field of Classification Search ........... 607/115–125
See application file for complete search history.

(56) References Cited

U.S. PATENT DOCUMENTS

| | | |
|---|---|---|
| 3,614,692 A | 10/1971 | Rozelle et al. |
| 4,131,759 A | 12/1978 | Felkel |
| 4,135,518 A | 1/1979 | Dutcher |
| 4,404,125 A | 9/1983 | Abolins et al. |
| 4,484,586 A | 11/1984 | McMickle et al. |
| 4,493,329 A | 1/1985 | Crawford et al. |
| 4,643,203 A | 2/1987 | Labbe |
| 4,869,970 A | 9/1989 | Gulla et al. |
| 5,056,516 A | 10/1991 | Spehr |
| 5,217,010 A | 6/1993 | Tsitlik et al. |
| 5,222,506 A | 6/1993 | Patrick et al. |
| 5,231,996 A | 8/1993 | Bardy et al. |
| 5,243,911 A | 9/1993 | Dow et al. |
| 5,246,014 A | 9/1993 | Williams et al. |
| 5,330,522 A | 7/1994 | Kreyenhagen |

(Continued)

FOREIGN PATENT DOCUMENTS

CN    1762510 A    4/2006

(Continued)

OTHER PUBLICATIONS

Gray, Robert W. et al., "Simple design changes to wires to substantially reduce MRI-induced heating at 1.5 T: implications for implanted leads", Magnetic Resonance Imaging 23 (2005) 887-891.

(Continued)

*Primary Examiner* — Rex R Holmes
(74) *Attorney, Agent, or Firm* — Faegre Baker Daniels LLP

(57) ABSTRACT

An implantable medical device lead includes an insulative lead body, an outer conductive coil extending through the lead body, and an inner conductive coil extending coaxially with the outer conductive coil. The outer conductive coil, which is coupled to a proximal electrode at a distal end of the outer conductive coil, has a first outer conductive coil diameter. The inner conductive coil is coupled to a distal electrode at a distal end of the inner conductive coil. The inner conductive coil includes a filar having a filar diameter and a coil pitch that is about one to one and a half times the filar diameter. The inner conductive coil transitions from a first inner conductive coil diameter to a larger second inner conductive coil diameter between the proximal electrode and the distal electrode.

13 Claims, 4 Drawing Sheets

U.S. PATENT DOCUMENTS

| | | | |
|---|---|---|---|
| 5,378,234 A | 1/1995 | Hammerslag et al. |
| 5,387,199 A | 2/1995 | Siman et al. |
| 5,425,755 A | 6/1995 | Doan |
| 5,456,707 A | 10/1995 | Giele |
| 5,483,022 A | 1/1996 | Mar |
| 5,522,872 A | 6/1996 | Hoff |
| 5,522,875 A | 6/1996 | Gates et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,618,208 A | 4/1997 | Crouse et al. |
| 5,728,149 A * | 3/1998 | Laske et al. ............... 607/122 |
| 5,760,341 A | 6/1998 | Laske et al. |
| 5,800,496 A | 9/1998 | Swoyer et al. |
| 5,810,887 A | 9/1998 | Accorti, Jr. et al. |
| 5,833,715 A * | 11/1998 | Vachon et al. ............... 607/120 |
| 5,935,159 A | 8/1999 | Cross, Jr. et al. |
| 5,957,970 A | 9/1999 | Shoberg et al. |
| 5,968,087 A | 10/1999 | Hess et al. |
| 6,057,031 A | 5/2000 | Breme et al. |
| 6,078,840 A | 6/2000 | Stokes |
| 6,106,522 A | 8/2000 | Fleischman et al. |
| 6,143,013 A | 11/2000 | Samson et al. |
| 6,178,355 B1 | 1/2001 | Williams et al. |
| 6,208,881 B1 | 3/2001 | Champeau |
| 6,249,708 B1 | 6/2001 | Nelson et al. |
| 6,256,541 B1 | 7/2001 | Heil et al. |
| 6,289,250 B1 | 9/2001 | Tsuboi et al. |
| 6,295,476 B1 | 9/2001 | Schaenzer |
| 6,400,992 B1 | 6/2002 | Borgersen et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,721,604 B1 | 4/2004 | Robinson et al. |
| 6,813,251 B1 | 11/2004 | Garney et al. |
| 6,850,803 B1 | 2/2005 | Jimenez et al. |
| 6,854,994 B2 | 2/2005 | Stein et al. |
| 6,920,361 B2 | 7/2005 | Williams |
| 6,925,334 B1 | 8/2005 | Salys |
| 6,949,929 B2 | 9/2005 | Gray et al. |
| 6,978,185 B2 | 12/2005 | Osypka |
| 6,993,373 B2 | 1/2006 | Vrijheid et al. |
| 6,999,821 B2 | 2/2006 | Jenney et al. |
| 7,013,180 B2 | 3/2006 | Dublin et al. |
| 7,013,182 B1 | 3/2006 | Krishnan |
| 7,123,013 B2 | 10/2006 | Gray |
| 7,138,582 B2 | 11/2006 | Lessar et al. |
| 7,174,219 B2 | 2/2007 | Wahlstrand et al. |
| 7,174,220 B1 | 2/2007 | Chitre et al. |
| 7,205,768 B2 | 4/2007 | Schulz et al. |
| 7,363,090 B2 | 4/2008 | Halperin et al. |
| 7,388,378 B2 | 6/2008 | Gray et al. |
| 7,389,148 B1 | 6/2008 | Morgan |
| 7,610,101 B2 | 10/2009 | Wedan et al. |
| 7,765,005 B2 | 7/2010 | Stevenson |
| 7,917,213 B2 | 3/2011 | Bulkes et al. |
| 8,103,360 B2 | 1/2012 | Foster |
| 8,170,688 B2 | 5/2012 | Wedan et al. |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0050680 A1 | 3/2003 | Gibson et al. |
| 2003/0063946 A1 | 4/2003 | Williams et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064173 A1 | 4/2004 | Hine et al. |
| 2004/0088033 A1 | 5/2004 | Smits et al. |
| 2004/0122490 A1 | 6/2004 | Reinke et al. |
| 2004/0162600 A1 | 8/2004 | Williams |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0246007 A1 | 11/2005 | Sommer et al. |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0041294 A1 | 2/2006 | Gray |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293737 A1 | 12/2006 | Krishman |
| 2007/0106332 A1 | 5/2007 | Denker et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0058902 A1 | 3/2008 | Gray et al. |
| 2008/0125754 A1 | 5/2008 | Beer et al. |
| 2008/0129435 A1 | 6/2008 | Gray |
| 2008/0132986 A1 | 6/2008 | Gray et al. |
| 2008/0243218 A1 | 10/2008 | Bottomley et al. |
| 2008/0262584 A1 | 10/2008 | Bottomley et al. |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0198314 A1 | 8/2009 | Foster et al. |
| 2009/0281608 A1 | 11/2009 | Foster |
| 2010/0010602 A1 | 1/2010 | Wedan et al. |
| 2010/0234929 A1 | 9/2010 | Scheuermann |
| 2010/0331936 A1 | 12/2010 | Perrey et al. |
| 2011/0093054 A1 | 4/2011 | Ameri et al. |
| 2011/0160828 A1 | 6/2011 | Foster et al. |
| 2011/0238146 A1 | 9/2011 | Wedan et al. |
| 2012/0022356 A1 | 1/2012 | Olsen et al. |
| 2012/0109270 A1 | 5/2012 | Foster |

FOREIGN PATENT DOCUMENTS

| | | |
|---|---|---|
| CN | 101039619 A | 9/2007 |
| EP | 0897997 B1 | 2/2003 |
| JP | 2004141679 A | 5/2004 |

| | | | |
|---|---|---|---|
| JP | 2005501673 A | 1/2005 |
| JP | 2005515852 A | 6/2005 |
| JP | 2005515854 A | 6/2005 |
| WO | WO03089045 A2 | 10/2003 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |

OTHER PUBLICATIONS

International Search Report and Written Opinion issued in PCT/US2008/085518 on Oct. 29, 2009, 15 pages.

International Search Report and Written Opinion issued in PCT/US2010/024062, mailed Sep. 27, 2010.

International Search Report and Written Opinion issued in PCT/US2010/033686 on Aug. 10, 2010, 12 pages.

Invitation to Pay Additional Fees and Partial Search Report, dated Aug. 17, 2009, issued in PCT/US2008/085533, 6 pages.

Invitation to Pay Additional Fees and Partial Search Report, issued in PCT/US2010/024062, mailed May 7, 2010.

International Search Report and Written Opinion issued in PCT/US2009/032838, mailed May 4, 2009, 14 pages.

International Search Report and Written Opinion issued in PCT/US2009/038629, mailed Jun. 29, 2009, 11 pages.

* cited by examiner

MEDICAL DEVICE LEAD INCLUDING A FLARED CONDUCTIVE COIL

CROSS-REFERENCE TO RELATED APPLICATION

This application claims priority to Provisional Application No. 61/249,738, filed Oct. 8, 2009, which is herein incorporated by reference in its entirety.

TECHNICAL FIELD

The present invention relates to implantable medical devices. More particularly, the present invention relates to medical device lead constructions including a flared conductive coil.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

The present invention relates to an implantable medical device lead including an insulative lead body and an outer conductive coil extending through the lead body. The outer conductive coil, which is coupled to a proximal electrode at a distal end of the outer conductive coil, has an outer conductive coil diameter. An inner conductive coil, which extends coaxially with the outer conductive coil, is coupled to a distal electrode at a distal end of the inner conductive coil. The inner conductive coil includes a filar having a filar diameter and a coil pitch that is less than about 1.5 times the filar diameter. The inner conductive coil transitions from a first inner conductive coil diameter to a larger second inner conductive coil diameter between the proximal electrode and the distal electrode.

In another aspect, the present invention relates to an implantable medical device lead including an insulative lead body, an outer conductive coil extending through the lead body, and an inner conductive coil extending coaxially with the outer conductive coil. The outer conductive coil has an outer conductive coil diameter and is coupled to a proximal electrode at a distal end of the outer conductive coil. The inner conductive coil is coupled to a distal electrode at a distal end of the inner conductive coil. The inner conductive coil transitions from a first inner conductive coil diameter to a larger second inner conductive coil diameter between the proximal electrode and the distal electrode. The inner conductive coil extends through the insulative lead body between the proximal and distal electrodes.

In a further aspect, the present invention relates to a medical device including a pulse generator, a lead including a lead body, an outer conductive coil extending through the lead body, and an inner conductive coil extending coaxially with the outer conductive coil. The outer conductive coil, which has an outer conductive coil diameter, includes a proximal end and a distal end and is configured to connect to the pulse generator at the proximal end and is coupled to a proximal electrode at the distal end. The inner conductive coil, which includes a proximal end and a distal end, is configured to connect to the pulse generator at the proximal end and is coupled to a distal electrode at the distal end. The inner conductive coil transitions from a first inner conductive coil diameter to a larger second inner conductive coil diameter between the proximal electrode and the distal electrode. The inner conductive coil extends through the insulative lead body between the proximal and distal electrodes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
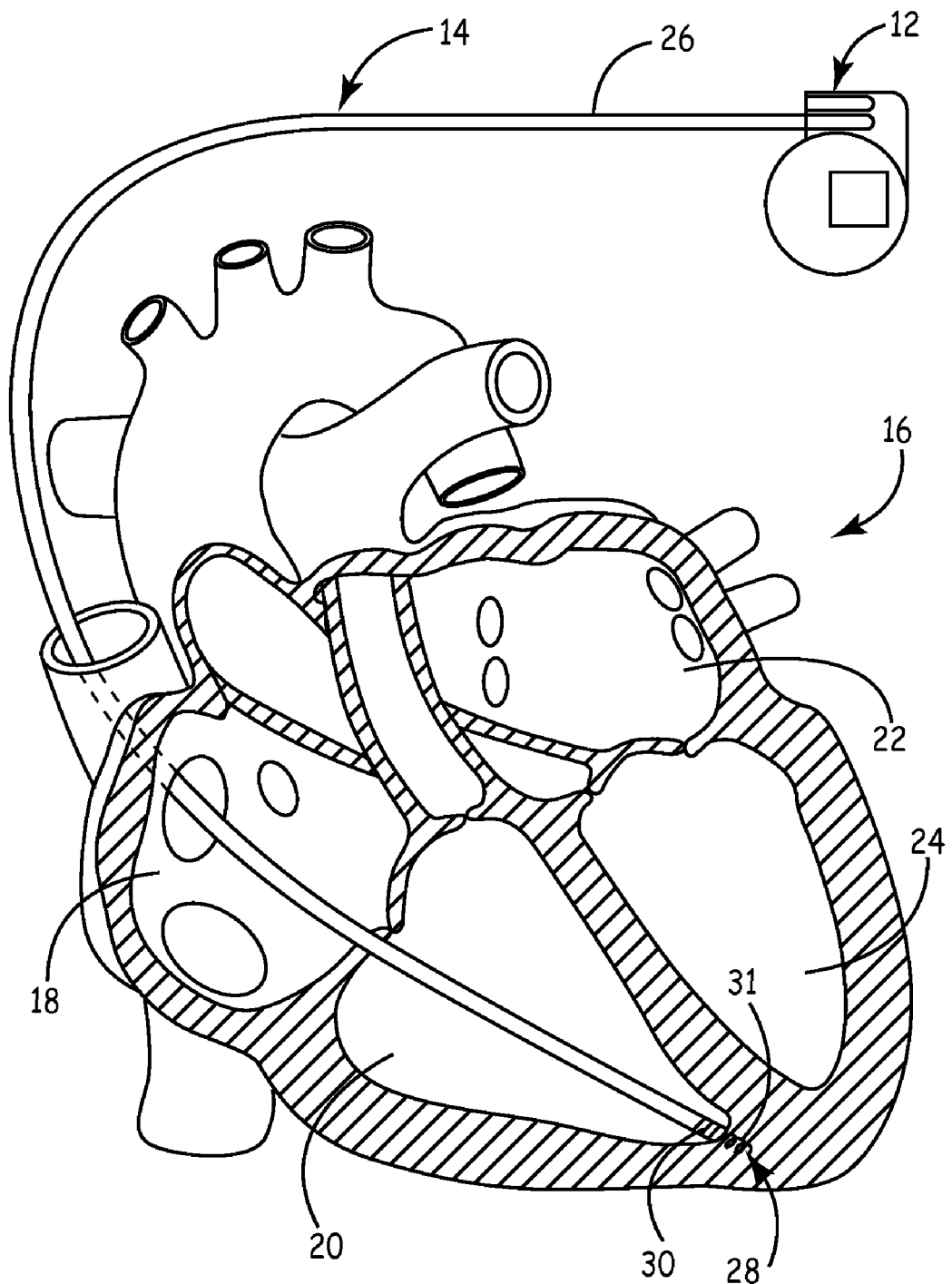
FIG. 1 is a schematic view of a cardiac rhythm management system including a pulse generator coupled to a lead deployed in a patient's heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an illustrative medical device 12 having with a lead implanted within the body of a patient. In the illustrative embodiment depicted, the medical device 12 comprises a pulse generator implanted within the body. The pulse generator 12 is coupled to a lead 14 inserted into the patient's heart 16. The heart 16 includes a right atrium 18, a right ventricle 20, a left atrium 22, and a left ventricle 24. The pulse generator 12 can be implanted subcutaneously within the body, typically at a location such as in the patient's chest or abdomen, although other implantation locations are possible.

A proximal section 26 of the lead 14 can be coupled to or formed integrally with the pulse generator 12. A distal section 28 of the lead 14, in turn, can be implanted at a desired location in or near the heart 16 such as in the right ventricle 20, as shown. In use, electrodes 30 and 31 on the distal section 28 of the lead 14 may provide therapy to the patient in the form of an electrical current to the heart 16. In certain embodiments, for example, electrodes 30 and 31 may be provided as part of a cardiac lead 14 used to treat bradycardia, tachycardia, or other cardiac arrhythmias.

Although the illustrative embodiment depicts only a single lead 14 inserted into the patient's heart 16, in other embodiments multiple leads can be utilized so as to electrically stimulate other areas of the heart 16. In some embodiments, for example, the distal section of a second lead (not shown) may be implanted in the right atrium 18. In addition, or in lieu, another lead may be implanted in or near the left side of the heart 16 (e.g., in the coronary veins) to stimulate the left side of the heart 16. Other types of leads such as epicardial leads may also be utilized in addition to, or in lieu of, the lead 14 depicted in FIG. 1.

During operation, the lead 14 can be configured to convey electrical signals between the pulse generator 12 and the heart 16. For example, in those embodiments where the pulse generator 12 is a pacemaker, the lead 14 can be utilized to deliver electrical therapeutic stimulus for pacing the heart 16. For example, in the treatment of bradycardia or tachycardia, the pulse generator 12 can be utilized to deliver electrical stimulus in the form of pacing pulses to the heart 16. In other embodiments in which the pulse generator 12 is an implantable cardiac defibrillator, the lead 14 can be utilized to deliver electric shocks to the heart 16 in response to an event such as a heart attack or arrhythmia. In some embodiments, the pulse generator 12 includes both pacing and defibrillation capabilities.

When the pulse generator 12 is subjected to a magnetic field from an MRI scanner or other external magnetic source, electromagnetic radiation is produced within the body that can be picked up by the lead 14 and transferred to the lead electrodes 30 and 31 in contact with the body tissue. This electromagnetic radiation can cause heating at the interface of the lead electrode 30 and 31 and body tissue, and can interfere with the therapeutic electrical currents transmitted by the pulse generator 12 through the lead 14.

Figure 2:
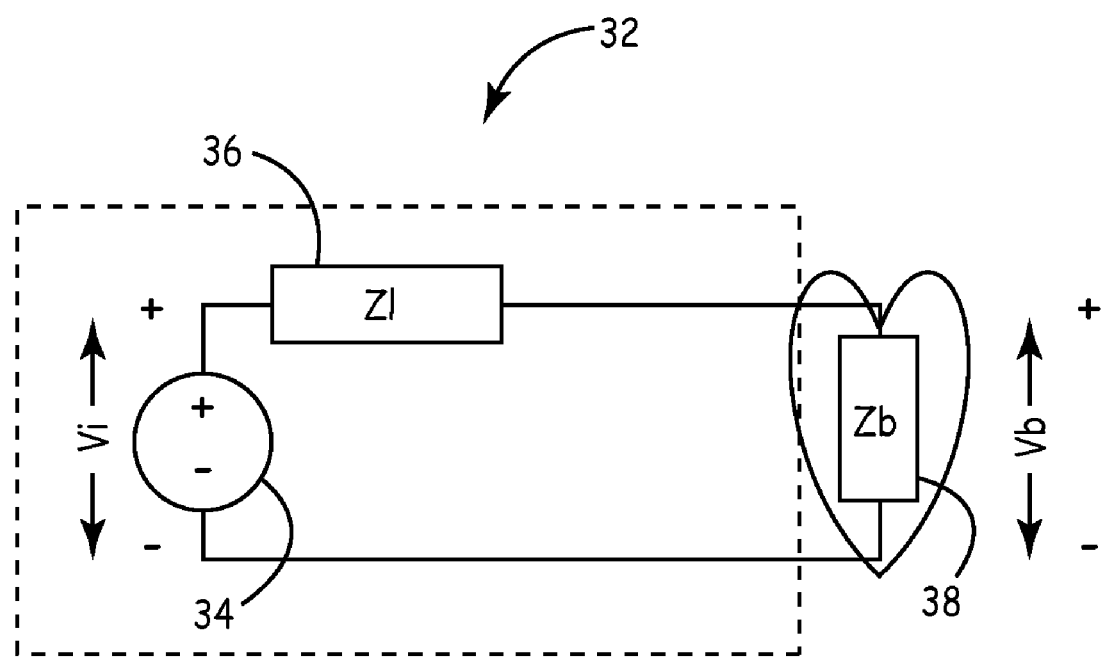
FIG. 2 is a schematic view showing a simplified equivalence circuit for the lead of FIG. 1.

FIG. 2 is a schematic view showing a simplified equivalence circuit 32 for the lead 14 of FIG. 1, representing the RF energy picked up on the lead 14 from RF electromagnetic energy produced by an MRI scanner. As shown in FIG. 2, Vi 34 in the circuit 32 represents an equivalent source of energy picked up by the lead 14 from the MRI scanner. During magnetic resonance imaging, the length of the lead 14 functions similar to an antenna, receiving the RF energy that is transmitted into the body from the MRI scanner. Voltage (Vi) 34 in FIG. 2 may represent, for example, the resultant voltage received by the lead 14 from the RF energy. The RF energy picked up by the lead 14 may result, for example, from the rotating RF magnetic field produced by an MRI scanner, which generates an electric field in the plane perpendicular to the rotating magnetic field vector in conductive tissues. The tangential components of these electric fields along the length of the lead 14 couple to the lead 14. The voltage (Vi) 34 is thus equal to the integration of the tangential electric field (i.e., the line integral of the electric field) along the length of the lead 14.

The Zl parameter 36 in the circuit 32 represents the equivalent impedance exhibited by the lead 14 at the RF frequency of the MRI scanner. The impedance value Zl 36 may represent, for example, the equivalent impedance resulting from the parallel inductance and the coil turn by turn capacitance exhibited by the lead 14 at an RF frequency of 64 MHz for a 1.5 Tesla MRI scanner, or at an RF frequency of 128 MHz for a 3 Tesla MRI scanner. The impedance Zl of the lead 14 is a complex quantity having a real part (i.e., resistance) and an imaginary part (i.e., reactance).

Zb 38 in the circuit 32 may represent the impedance of the body tissue at the point of lead contact. As indicated by Zb 38, there is an impedance at the point of contact of the lead electrodes 30 and 31 to the surrounding body tissue within the heart 16. The resulting voltage Vb delivered to the body tissue may be related by the following formula:

$$Vb = ViZb/(Zb+Zl).$$

The temperature at the tip of the lead 14 where contact is typically made to the surrounding tissue is related in part to the power dissipated at Zb 38, which, in turn, is related to the square of Vb. To minimize temperature rises resulting from the power dissipated at 38, it is thus desirable to minimize Vi 34 while also maximizing the impedance Zl 36 of the lead 14. In some embodiments, the impedance Zl 36 of the lead 14 can be increased at the RF frequency of the MRI scanner, which aids in reducing the energy dissipated into the surrounding body tissue at the point of contact.

In some embodiments, the impedance of the lead 14 can be increased by adding inductance to the lead 14 and/or by a suitable construction technique. For example, the inductance of the lead 14 can be increased by increasing the diameter of the conductor coil(s) and/or by decreasing the pitch of the conductor coil(s) used to supply electrical energy to the electrodes 30 and 31. Decreasing the coil pitch may result in increasing capacitance between successive turns of the coil (i.e., coil turn by turn capacitance). The parallel combination of inductance (from the helical shape of the coil) and the turn by turn capacitance constitutes a resonance circuit. For a helically coiled lead construction, if the resonance frequency of the lead is above the RF frequency of the MRI, then the helical coil acts as an inductor. For an inductor, increasing the cross section of the coil area and/or reducing the coil pitch increases the inductance and, as a result, increases the impedance of the lead 14.

Similar to an antenna, the energy pickup from a lead is related to its resonance length with respect to the wavelength of the frequency of interest. For example, for a dipole antenna, the antenna is considered tuned, or at resonance, when the antenna length is half the wavelength or an integer multiple of the wavelength. At resonance lengths, the energy pickup of the antenna is maximized. In a similar manner, and in some embodiments, the lead 14 can be detuned so as to prevent resonance within the lead 14, and thus minimize the voltage Vi. For the illustrative embodiment shown in FIG. 1, for example, the lead 14 functions as an antenna having a resonance frequency at length L=integer x $\lambda/2$. In some embodiments, the length of the lead 14 and/or the construction parameters of the lead 14 affecting the wavelength can be chosen so as to avoid resonance within the lead 14.

Figure 3:
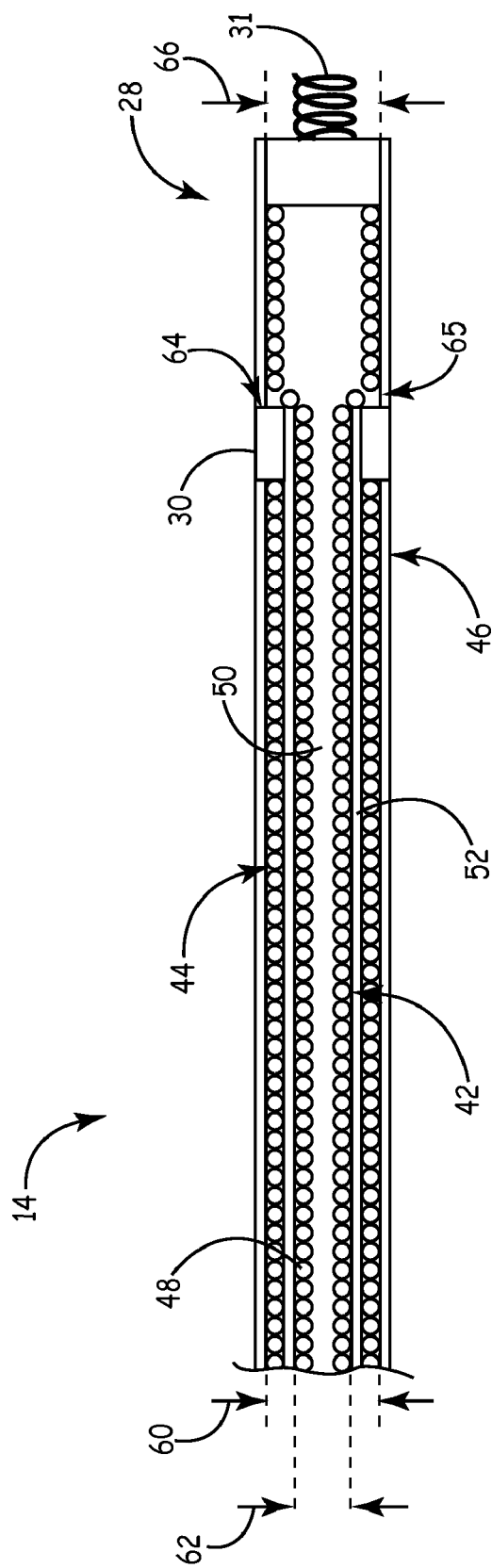
FIG. 3 is a cross-sectional view of a distal end of a lead according to an embodiment of the present invention including an inner conductive coil with a flared diameter between ring and tip electrodes at the distal end.

FIG. 3 is a cross-sectional view showing the interior construction of the distal end 28 of the lead 14 of FIG. 1 in accordance with an exemplary embodiment. In the embodiment of FIG. 3, the lead 14 includes an inner conductive coil 42, an outer conductive coil 44, and an insulation layer 46 disposed radially about the outer conductive coil 44.

In the illustrated embodiment of FIG. 3, the inner conductive coil 42 comprises a helically-shaped conductive coil including one or more filars 48 that are tightly wound together to form an inner conductor used to deliver electrical stimulus energy through the lead 14. In one embodiment, for example, the inner conductive coil 42 comprises a single filar 48. In other embodiments, the inner conductive coil 42 can include a greater number of filar strands 48. In some embodiments, each of the filar strands 48 forming the inner conductive coil 42 can comprise a silver-filled MP35N wire having a silver content of about 10% to 28% by cross-sectional area. In certain embodiments, the pitch of the inner conductive coil 42 is about one to one and a half times the filar diameter of the inner conductive coil 42.

In some embodiments, the inner conductive coil 42 has a hollowed configuration, including an interior lumen 50 extending through the inner conductive coil 42 and adapted to receive a stylet or guidewire that can be used to facilitate implantation of the lead 14 within the body. In certain embodiments, the inner conductive coil 42 can be fabricated by co-radially winding a number of wire filars about a mandrel having a diameter that is slightly greater than the diameter of the stylet or guidewire to be inserted into the lumen 50. To improve the torque characteristics of the wire 42, the wire filars 48 can be tightly wound together during fabrication of the wire 42 such that no gaps or spaces exist between the filar strands 48.

As further shown in FIG. 3, and in some embodiments, the outer conductive coil 44 is coaxially disposed about the inner conductive coil 42 and has a helically coiled configuration that extends along all or a portion of the length of the lead 14. The outer conductive coil 44 has an outer conductive coil diameter 60. In some embodiments, the outer conductive coil 44 has a single-filar construction formed from a single wound wire. In other embodiments, the outer conductor 44 has a multifilar construction formed from multiple, co-radially wound wire filars. In one embodiment, for example, the outer conductive coil 44 has a double-filar construction formed from two co-radially wound wire filars.

The outer conductive coil 44 can be spaced radially apart from the inner conductive coil 44, electrically isolating the outer conductive coil 44 from the inner conductive coil 42. In some embodiments, for example, the outer conductive coil 44 is electrically isolated from the inner conductive coil 42 so that the lead 14 can function as a multipolar lead. In certain embodiments, a second layer of insulation 52 interposed between the inner conductive coil 42 and the outer conductive coil 44 is further used to electrically isolate the conductive coils 42, 44 from each other. In some embodiments, for example, the second layer of insulation 52 may comprise a sheath made from silicon, polyurethane, or other suitable polymeric material.

In some embodiments, the outer conductive coil 44 is formed from a drawn-filled tube having an outer tubular layer of low-resistive metal or metal-alloy such as MP35N filled with an inner core of electrically conductive material such as silver. Once filled and drawn, the tube is then coiled into a helical shape and attached to the lead 14 using conventional techniques known in the art. In one embodiment, the outer conductive coil 44 comprises a silver-filled MP35N wire having a silver content of about 28% by cross-sectional area. In use, the relatively low resistance of the outer tubular metal or metal-alloy forming part of the outer conductive coil 44 can be used to offset the increased resistance imparted to the conductive coil 44 from using a smaller diameter wire, as discussed above. In some embodiments, the material or materials forming the outer conductive coil 44 can also be selected so as to impart greater flexibility to the conductive coil 44.

The outer conductive coil 44 may be formed from a material or materials different than the inner conductive coil 42 in order to impart greater resistance to the outer conductive coil 44 to aid in dissipating RF electromagnetic energy received during an MRI procedure. In one embodiment, for example, the wire filars forming the outer conductive coil 44 may comprise a silver-filled MP35N material having a silver content (by cross-sectional area) of about 28%, whereas the wire filars forming the inner conductive coil 42 may have a silver content (by cross-sectional area) lower than 28%.

The outer conductive coil 44 is coupled to proximal electrode 30 at a distal end of the outer conductive coil 44, and the inner conductive coil 42 is coupled to distal electrode 31 at a distal end of the inner conductive coil 42. In the embodiment shown, the electrode 30 is a ring electrode and the electrode 31 is an active fixation helix electrode that is coupled to the tissue of the heart 16 upon implantation. It will be appreciated, however, that the electrodes 30 and 31 can have other configurations. For example, the electrode 31 may be a tip electrode without a fixation mechanism. In other embodiments, the lead 14 can be configured with more or fewer electrodes.

As discussed above, the inductance of the lead 14 can be increased by increasing the diameter of the conductive coils 42 and 44. To increase the inductance of the outer conductive coil 44, the outer conductive coil diameter 60 can be maximized along the length of the lead 14 such that the outer conductive coil 44 is adjacent the outer insulation layer 46. The inner conductive coil 42 has a first inner conductive coil diameter 62 from the proximal end of the lead 14 to a distal end 64 of the proximal electrode 30. The inner conductive coil 42 then transitions or flares at transition section 65 to a second inner conductive coil diameter 66 on the distal end 64 of the proximal electrode 30. The transition section 65 is proximate to the distal end 64 of the electrode 30 to maximize the number of turns of the inner conductive coil 42 at the second conductive coil diameter 66.

To accommodate this transition, the layer of insulation 52 is terminated at the distal end 64 of the proximal electrode 30, thus opening the portion of the lead 14 between the electrodes 30 and 31 to the outer insulation layer 46. To maximize the diameter 66 of the inner conductive coil 42 between the electrodes 30 and 31, the inner conductive coil 42 may flare such that the inner conductive coil 42 is adjacent to the outer insulation layer 46. In some embodiments, the second inner conductive coil diameter 66 is substantially equal to the outer conductive coil diameter 60. In embodiments in which the electrode 31 is extendable and retractable, the second inner conductive coil diameter 66 may be slightly less than the outer conductive coil diameter 60 to accommodate the mechanism to effect extension and retraction of the electrode 31. In alternative embodiments, the inner conductive coil 42 flares from the first inner conductive coil diameter 62 to the second inner conductive coil diameter 66 more distal from the electrode 30 and more proximate to the electrode 31.

In some embodiments, the outer conductive coil diameter 60 is in the range of between about 0.050 to 0.075 inches. The overall diameter of the outer conductor coil 44 may be greater or lesser, however, depending on the type of lead employed, the configuration of the lead, as well as other factors. In some embodiments, the overall diameter of the lead 14 is in the range of between about 3 to 7 Fr, and more specifically, between about 5 to 6 Fr.

In some embodiments, the inner conductive coil 42 has a filar diameter of between about 0.001 to 0.006 inches. In certain embodiments, the first inner conductive coil diameter 62 is between about 0.015 to 0.030 inches. In some embodiments, the pitch of the inner conductive coil 42 is between about 0.001 to 0.018 inches. The dimensions of the inner conductor wire 42, including the filar diameter and the first inner conductive coil diameter 62 may vary, however.

Due to the increased diameter, the inner conductive coil 42 has an increased inductance between the electrodes 30 and 31. By increasing the inductance of the lead 14, and in particular the inductance of the inner conductive coil 42, the lead 14 is configured to block RF electromagnetic energy received during a magnetic resonance imaging procedure. This blocking of electromagnetic energy results in a reduction in heating of body tissue at the location of the electrode 31. The increase in inductance of the lead 14 also reduces the effects of the electromagnetic energy on the therapeutic electrical current delivered through the lead 14, and in some cases, may permit the lead 14 to continue to provide therapy during the MRI procedure. In some embodiments, for example, the increase in inductance of the lead 14 allows the lead 14 to function at normal device frequencies (e.g., 0.5 Hz to 500 Hz) while acting as a poor antenna at MRI frequencies.

While the illustrative lead 14 is described with respect to a cardiac lead for use in providing pacing to a patient's heart 16, the construction of the lead 14 may also be applicable to other medical devices that operate in the presence of electromagnetic fields. For example, the construction of the lead 14, including the inner and outer conductive coils 42, 44, may be used in neural leads adapted for use in neurological applications that utilize MRI imaging.

In addition, while the flaring has been described with respect to co-axial conductive coils 42, 44, lead conductors having other configurations may also be flared at the distal end to increase the impedance of the conductor. For example, in a tachy lead design, the lead conductors may not be co-axial in that the shocking cable/coil and pacing/sensing conductors may extend in parallel along the lead body. The shocking cable/coil may be coupled to a large diameter shocking coil at the distal end the lead. In some embodiments, the pacing/sensing conductors extend through the shocking coil and are flared within the shocking coil and connected to one or more pacing/sensing electrodes at a distal end.

Figure 4:
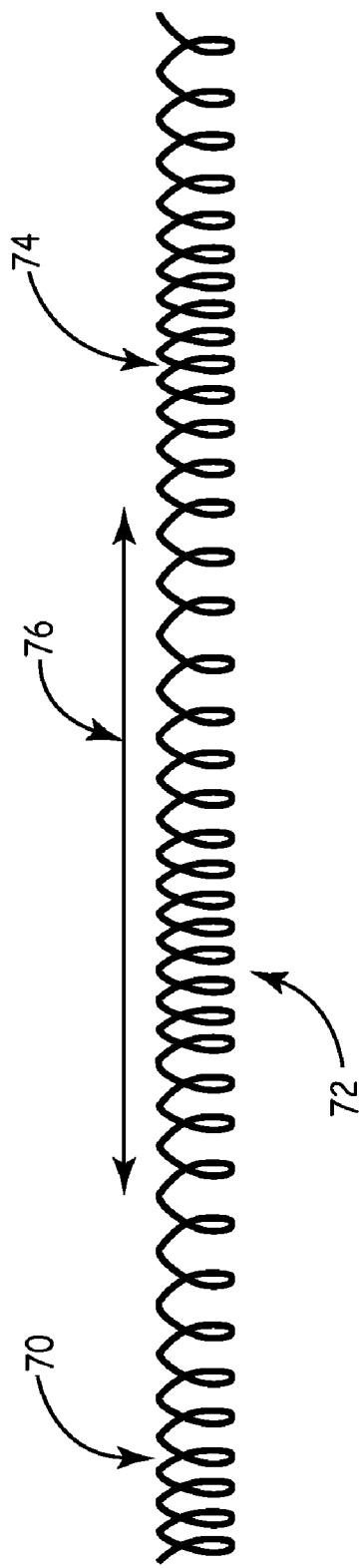
FIG. 4 is a plan view of a portion of a conductive coil having a variable pitch according to an embodiment of the present invention.

Furthermore, while the conductive coils 42, 44 of the lead 14 have been shown and described as having a constant pitch, the conductive coils 42 and/or 44 may alternatively have a variable pitch along the length of the lead 14. FIG. 4 is a plan view of a portion of a conductive coil having a variable pitch according to some embodiments. The varying pitch creates high impedance frequency dependent points 70, 72, and 74 along the length of the lead 14, reducing the RF pickup energy of the conductive coils 42, 44. In some embodiments, the variance of pitch along portions of the conductive coils 42, 44 may follow a particular function. Also, in some embodiments, the pitch pattern is repeated several times along the length of the lead 14 such that the pitch pattern covers a lead length of less than ¼ of the wavelength of the highest frequency to be filtered. In the embodiment shown in FIG. 4, the pitch pattern includes a repeating pattern element 76, but patterns including other repeating patterns are also contemplated. During an MRI scan, this detuning of the lead 14 prevents the lead 14 from approaching the antenna resonance length, thus minimizing the RF energy picked up by the conductive coils 42 and 44. One exemplary approach to varying the pitch of the conductive coils 42 and 44 is described in U.S. Patent App. Pub. 2009/0149933, entitled "Implantable Lead Having a Variable Coil Conductor Pitch," which is hereby incorporated by reference in its entirety.

In one example implementation, the MRI-induced signal response of a lead 14 including conductive coils 42 and 44 having a variable pitch and a flared inner conductive coil 42 was compared to a similar lead having a non-flared inner conductive coil. In each embodiment, the outer conductive coil diameter 60 was about 0.052 in (0.132 cm) and the first inner conductive coil diameter 62 was about 0.027 in (0.069 cm). The second inner conductive coil diameter 66 (i.e., the flared diameter) was about 0.052 in (0.027 cm). The pitch of the conductive coils 42, 44 were varied between about 0.005 in (0.013 cm) and about 0.015 in (0.038 cm), while the pitch of the inner conductive coil 42 after flaring was held constant at about 0.006 in (0.015 cm). The length of the repeating pattern element 76 was varied for each of the embodiments tested, as shown in Table 1 below. The leads tested were exposed to an MRI field for 50-80 seconds. The temperature increase resulting from this MRI field exposure, measured at the lead tip electrode, are set forth in Table 1 for a lead with a flared inner conductive coil 42 and a lead having a similar configuration with a non-flared inner conductive coil.

TABLE 1

| Electrode Temperature Increase | | | |
|---|---|---|---|
| Inner Conductive Coil-Repeating Pattern Element Length | Outer Conductive Coil-Repeating Pattern Element Length | Electrode Temperature Increase-Non-flared Inner Conductive Coil | Electrode Temperature Increase-Flared Inner Conductive Coil |
| 4.0 cm | 1.7 cm | 6.69° C. | 5.27° C. |
| 2.75 cm | 2.75 cm | 4.84° C. | 3.00° C. |
| 1.77 cm | 1.77 cm | 20.7° C. | 3.58° C. |

In summary, the present invention relates to an implantable medical device lead including an insulative lead body and an outer conductive coil extending through the lead body. The outer conductive coil, which is coupled to a proximal electrode at a distal end of the outer conductive coil, has an outer conductive coil diameter. An inner conductive coil, which extends coaxially with the outer conductive coil, is coupled to a distal electrode at a distal end of the inner conductive coil. The inner conductive coil includes a filar having a filar diameter and a coil pitch that is about one to one and a half times the filar diameter. The inner conductive coil transitions from a first inner conductive coil diameter to a larger second inner conductive coil diameter between the proximal electrode and the distal electrode. In some embodiments, the second inner conductive coil diameter is substantially equal to the outer conductive coil diameter. The increased diameter of the inner conductive coil reduces the amount of energy that is transferred to the distal electrode during MRI procedures, thereby reducing the amount of electrode heating.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:
1. An implantable medical device lead comprising:
an insulative lead body;
proximal and distal electrodes disposed on the insulative lead body;
an outer conductive coil extending through the lead body, the outer conductive coil coupled to the proximal elec- trode at a distal end of the outer conductive coil, wherein the outer conductive coil has an outer conductive coil diameter;

an inner conductive coil extending coaxially with the outer conductive coil, the inner conductive coil coupled to the distal electrode at a distal end of the inner conductive coil, the inner conductive coil comprising a filar having a filar diameter and a coil pitch that is about one to one and a half times the filar diameter, wherein the inner conductive coil transitions from a first inner conductive coil diameter to a larger second inner conductive coil diameter between the proximal electrode and the distal electrode; and an insulative layer disposed between the inner conductive coil and outer conductive coil, the insulative layer terminating at a distal side of the proximal electrode, wherein the inner conductive coil transitions from the first inner conductive coil diameter to the second inner conductive coil diameter adjacent the distal side of the proximal electrode.

2. The implantable medical device lead of claim 1, wherein the second inner conductive coil diameter is substantially equal to the outer conductive coil diameter.

3. The implantable medical device lead of claim 1, wherein the pitch of the inner conductive coil continuously varies along a length of the lead.

4. The implantable medical device lead of claim 1, wherein the proximal electrode comprises a ring electrode and the distal electrode comprises a tip electrode.

5. An implantable medical device lead comprising:
an insulative lead body;
proximal and distal electrodes disposed on the insulative lead body;
an outer conductive coil extending through the lead body, the outer conductive coil coupled to the proximal electrode at a distal end of the outer conductive coil, wherein the outer conductive coil has an outer conductive coil diameter;
an inner conductive coil extending coaxially with the outer conductive coil, the inner conductive coil coupled to the distal electrode at a distal end of the inner conductive coil, wherein the inner conductive coil transitions from a first inner conductive coil diameter to a larger second inner conductive coil diameter between the proximal electrode and the distal electrode, and wherein the inner conductive coil extends through the insulative lead body between the proximal and distal electrodes; and
an insulative layer disposed between the inner conductive coil and outer conductive coil, the insulative layer terminating at a distal side of the proximal electrode,
wherein the inner conductive coil transitions from the first inner conductive coil diameter to the second inner conductive coil diameter adjacent the distal side of the proximal electrode.

6. The implantable medical device lead of claim 5, wherein the second inner conductive coil diameter is substantially equal to the outer conductive coil diameter.

7. The implantable medical device lead of claim 5, wherein the inner conductive coil is adjacent the insulative lead body between the proximal and distal electrodes.

8. The implantable medical device lead of claim 5, wherein the inner conductive coil comprising a filar having a filar diameter and a coil pitch that is about one to one and a half times the filar diameter.

9. The implantable medical device lead of claim 8, wherein the pitch of the inner conductive coil continuously varies along a length of the lead.

10. A medical device, comprising:
a pulse generator; and
a lead including a lead body, proximal and distal electrodes disposed on the insulative lead body, an outer conductive coil extending through the lead body, an inner conductive coil extending coaxially with the outer conductive coil, and an insulative layer disposed between the inner conductive coil and outer conductive coil, the insulative layer terminating at a distal side of the proximal electrode,
the outer conductive coil including a proximal end and a distal end and configured to connect to the pulse generator at the proximal end and coupled to a proximal electrode at the distal end, wherein the outer conductive coil has an outer conductive coil diameter,
the inner conductive coil including a proximal end and a distal end, the inner conductive coil configured to connect to the pulse generator at the proximal end and coupled to a distal electrode at the distal end, wherein the inner conductive coil transitions from a first inner conductive coil diameter to a larger second inner conductive coil diameter between the proximal electrode and the distal electrode, and wherein the inner conductive coil extends through the insulative lead body between the proximal and distal electrodes
wherein the inner conductive coil transitions from the first inner conductive coil diameter to the second inner conductive coil diameter adjacent the distal side of the proximal electrode.

11. The medical device of claim 10, wherein the second inner conductive coil diameter is substantially equal to the outer conductive coil diameter.

12. The medical device of claim 10, wherein the inner conductive coil comprising a filar having a filar diameter and a coil pitch that is about one to one and a half times the filar diameter.

13. The medical device of claim 12, wherein the pitch of the inner conductive coil continuously varies along a length of the lead.

* * * * *